(12) United States Patent
Watson, Jr.

(10) Patent No.: US 7,790,945 B1
(45) Date of Patent: Sep. 7, 2010

(54) WOUND DRESSING WITH ABSORPTION AND SUCTION CAPABILITIES

(75) Inventor: Richard L. Watson, Jr., McPherson, KS (US)

(73) Assignee: KCI Licensing, Inc., San Antonio, TX (US)

( * ) Notice: Subject to any disclaimer, the term of this patent is extended or adjusted under 35 U.S.C. 154(b) by 947 days.

(21) Appl. No.: 10/818,468

(22) Filed: Apr. 5, 2004

(51) Int. Cl.
  *A61F 13/00* (2006.01)
  *A61M 1/00* (2006.01)
  *A61M 35/00* (2006.01)

(52) U.S. Cl. .............................. 602/43; 602/47; 602/53; 604/313; 604/289; 604/540

(58) Field of Classification Search .................. 604/289, 604/304–308, 313, 543, 540; 602/48, 41–43, 602/44, 45, 46, 47, 50, 51, 52, 53
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,026,874 | A | 3/1962 | Stevens |
| 3,066,672 | A | 12/1962 | Crosby, Jr. et al. |
| 3,089,492 | A | 5/1963 | Owens |
| 3,142,298 | A | 7/1964 | Koski et al. |
| 3,367,332 | A | 2/1968 | Groves |
| 3,472,230 | A | 10/1969 | Fogarty |
| 3,520,300 | A | 7/1970 | Flower, Jr. |
| 3,568,675 | A | 3/1971 | Harvey |
| 3,648,692 | A | 3/1972 | Wheeler |

(Continued)

FOREIGN PATENT DOCUMENTS

AU  550575 A1  8/1982

(Continued)

OTHER PUBLICATIONS

Louis C. Argenta, MD and Michael J. Morykwas, PhD; "Vacuum-Assisted Closure: A New Method for Wound Control and Treatment: Clinical Experience"; Annals of Plastic Surgery, vol. 38, No. 6, Jun. 1997; pp. 563-576.

(Continued)

*Primary Examiner*—Patricia M Bianco
*Assistant Examiner*—Ophelia Hawthorne

(57) ABSTRACT

A wound dressing having a suction member adaptable for connection to a source of vacuum pressure. The wound dressing preferably has a hydrophobic or biodegradable base layer and one or more absorptive layers for absorbing fluid from the wound. The absorptive layers are preferably quilted with patches containing desiccant, adsorbent, or absorbent material. Alternatively, the wound dressing may allow fluid to pass through the suction member. A semi-permeable cover is provided for allowing the wound to breathe while protecting the wound from undesirable substances such as bacteria, viruses, or fluids. The cover may have a bladder for distributing contact pressure away from the wound. Various sensors may be provided in the wound dressing for sensing various physiological parameters in the wound, such as oxygen saturation, blood pressure, respiratory rate, blood glucose, and serous fluid turbidity. Medicine may also be applied to the wound through the wound dressing.

25 Claims, 7 Drawing Sheets

U.S. PATENT DOCUMENTS

| | | | |
|---|---|---|---|
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,360 A | 4/1981 | Perez | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,409,974 A | 10/1983 | Freedland | |
| 4,419,097 A | 12/1983 | Rowland | |
| 4,421,583 A | 12/1983 | Aldred et al. | 156/167 |
| 4,444,545 A | 4/1984 | Sanders et al. | |
| 4,464,172 A | 8/1984 | Lichtenstein | |
| 4,465,485 A | 8/1984 | Kashmer et al. | |
| 4,468,219 A | 8/1984 | George et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,533,352 A | 8/1985 | Van Beek | |
| 4,536,217 A | 8/1985 | Loth et al. | 106/122 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,753,230 A | 6/1988 | Carus et al. | 128/156 |
| 4,758,220 A | 7/1988 | Sundblom et al. | |
| 4,787,888 A | 11/1988 | Fox | |
| 4,820,291 A | 4/1989 | Terauchi et al. | |
| 4,826,494 A | 5/1989 | Richmond et al. | |
| 4,838,883 A | 6/1989 | Matsuura | |
| 4,840,187 A | 6/1989 | Brazier | |
| 4,848,364 A | 7/1989 | Bosman | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt et al. | |
| 4,930,997 A | 6/1990 | Bennett | |
| 4,941,882 A | 7/1990 | Ward et al. | |
| 4,953,565 A | 9/1990 | Tachibana et al. | |
| 4,957,484 A | 9/1990 | Murtfeldt | |
| 4,969,880 A * | 11/1990 | Zamierowski | 604/305 |
| 4,985,019 A | 1/1991 | Michelson | |
| 4,996,128 A | 2/1991 | Aldecoa et al. | |
| 5,002,541 A | 3/1991 | Conkling et al. | |
| 5,037,397 A | 8/1991 | Kalt et al. | |
| 5,073,172 A | 12/1991 | Fell | |
| 5,086,170 A | 2/1992 | Luheshi et al. | |
| 5,092,858 A | 3/1992 | Benson et al. | |
| 5,100,395 A | 3/1992 | Rosenberg | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,180,375 A | 1/1993 | Feibus | |
| 5,211,639 A * | 5/1993 | Wilk | 604/317 |
| 5,215,522 A | 6/1993 | Page et al. | |
| 5,232,453 A | 8/1993 | Plass et al. | |
| 5,254,084 A | 10/1993 | Geary | |
| 5,261,893 A | 11/1993 | Zamierowski | |
| 5,278,100 A | 1/1994 | Doan et al. | |
| 5,279,550 A | 1/1994 | Habib et al. | |
| 5,279,602 A | 1/1994 | Middaugh et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,356,386 A | 10/1994 | Goldberg et al. | |
| 5,358,494 A | 10/1994 | Svedman | |
| 5,419,769 A | 5/1995 | Devlin et al. | |
| 5,429,601 A | 7/1995 | Conley et al. | |
| 5,437,622 A | 8/1995 | Carion | |
| 5,437,651 A | 8/1995 | Todd et al. | |
| 5,449,347 A | 9/1995 | Preen et al. | |
| 5,458,582 A | 10/1995 | Nakao | |
| 5,466,229 A | 11/1995 | Elson et al. | |
| 5,522,808 A | 6/1996 | Skalla | |
| 5,527,293 A | 6/1996 | Zamierowski | |
| 5,549,584 A | 8/1996 | Gross | |
| 5,549,585 A | 8/1996 | Maher et al. | |
| 5,556,375 A | 9/1996 | Ewall | |
| 5,565,210 A | 10/1996 | Rosenthal et al. | 424/426 |
| 5,599,292 A | 2/1997 | Yoon | |
| 5,607,388 A | 3/1997 | Ewall | |
| 5,628,735 A | 5/1997 | Skow | |
| 5,634,893 A | 6/1997 | Rishton | |
| 5,636,643 A | 6/1997 | Argenta et al. | |
| 5,645,081 A | 7/1997 | Argenta et al. | |
| 5,678,564 A | 10/1997 | Lawrence et al. | |
| 5,679,371 A | 10/1997 | Tanihara et al. | 424/443 |
| 5,681,579 A | 10/1997 | Freeman | 424/448 |
| 5,700,477 A | 12/1997 | Rosenthal et al. | 424/426 |
| 5,733,337 A | 3/1998 | Carr, Jr. et al. | 623/11 |
| 5,741,237 A | 4/1998 | Walker | |
| 5,759,830 A | 6/1998 | Vacanti et al. | 435/180 |
| 5,776,119 A | 7/1998 | Bilbo et al. | |
| 5,827,246 A | 10/1998 | Bowen | |
| 5,836,970 A | 11/1998 | Pandit | 606/213 |
| 5,885,237 A | 3/1999 | Kadash et al. | 602/48 |
| 5,891,111 A | 4/1999 | Ismael | |
| 5,928,174 A | 7/1999 | Gibbins | 602/41 |
| 5,944,703 A | 8/1999 | Dixon et al. | |
| 5,945,004 A | 8/1999 | Ohira et al. | |
| 5,974,344 A | 10/1999 | Shoemaker, III | |
| 5,977,428 A * | 11/1999 | Bozigian et al. | 602/48 |
| 5,981,822 A | 11/1999 | Addison | 602/41 |
| 6,024,731 A | 2/2000 | Seddon et al. | |
| 6,071,267 A | 6/2000 | Zamierowski | |
| 6,077,526 A | 6/2000 | Scully et al. | 424/443 |
| 6,095,998 A | 8/2000 | Osborn, III et al. | 604/11 |
| 6,126,675 A | 10/2000 | Shchervinsky et al. | |
| 6,135,116 A | 10/2000 | Vogel et al. | |
| 6,142,982 A | 11/2000 | Hunt et al. | 604/313 |
| 6,152,902 A | 11/2000 | Christian et al. | |
| 6,175,053 B1 | 1/2001 | Tsubouchi | 602/43 |
| 6,179,804 B1 * | 1/2001 | Satterfield | 604/23 |
| 6,210,360 B1 | 4/2001 | Kong | |
| 6,235,009 B1 | 5/2001 | Skow | |
| 6,241,747 B1 | 6/2001 | Ruff | |
| 6,245,961 B1 | 6/2001 | Roxendal et al. | 604/367 |

| | | | |
|---|---|---|---|
| 6,248,112 B1 | 6/2001 | Gambale et al. | |
| 6,287,316 B1 | 9/2001 | Agarwal et al. | |
| 6,334,064 B1 | 12/2001 | Fiddian-Green | |
| 6,345,623 B1 | 2/2002 | Heaton et al. | |
| 6,352,525 B1 | 3/2002 | Wakabayashi | |
| 6,356,782 B1 | 3/2002 | Sirimanne et al. | 600/431 |
| 6,365,149 B2 | 4/2002 | Vyakarnam et al. | 424/93.1 |
| 6,398,767 B1 * | 6/2002 | Fleischmann | 604/313 |
| 6,411,853 B1 | 6/2002 | Millot et al. | 607/50 |
| 6,488,643 B1 | 12/2002 | Tumey et al. | |
| 6,493,568 B1 | 12/2002 | Bell et al. | |
| 6,503,450 B1 | 1/2003 | Afzal et al. | |
| 6,514,515 B1 | 2/2003 | Willams | 424/424 |
| 6,530,472 B2 | 3/2003 | Hacikyan | |
| 6,536,291 B1 | 3/2003 | Gysling et al. | |
| 6,548,569 B1 | 4/2003 | Williams et al. | |
| 6,553,998 B2 | 4/2003 | Heaton et al. | |
| 6,557,704 B1 | 5/2003 | Randolph | |
| 6,566,575 B1 | 5/2003 | Stickels et al. | 602/41 |
| 6,648,862 B2 * | 11/2003 | Watson | 604/319 |
| 6,685,681 B2 * | 2/2004 | Lockwood et al. | 604/305 |
| 6,693,180 B2 | 2/2004 | Lee et al. | 536/20 |
| 6,695,823 B1 | 2/2004 | Lina et al. | |
| 6,752,794 B2 | 6/2004 | Lockwood et al. | |
| 6,755,807 B2 | 6/2004 | Rick, Jr. | |
| 6,764,462 B2 | 7/2004 | Rick, Jr. | |
| 6,767,334 B1 | 7/2004 | Randolph | |
| 6,800,074 B2 | 10/2004 | Henley et al. | |
| 6,814,079 B2 | 11/2004 | Heaton et al. | |
| 6,840,960 B2 | 1/2005 | Bubb | |
| 6,855,153 B2 | 2/2005 | Saadat | |
| 6,856,821 B2 * | 2/2005 | Johnson | 600/345 |
| 6,860,873 B2 | 3/2005 | Allen et al. | |
| 6,994,702 B1 * | 2/2006 | Johnson | 606/9 |
| 7,070,584 B2 * | 7/2006 | Johnson et al. | 604/313 |
| 7,182,758 B2 | 2/2007 | McCraw | |
| 7,361,184 B2 * | 4/2008 | Joshi | 606/213 |
| 2001/0001835 A1 | 5/2001 | Greene, Jr. et al. | 623/1.23 |
| 2002/0077661 A1 | 6/2002 | Saadat | |
| 2002/0095218 A1 | 7/2002 | Carr, Jr. et al. | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0150604 A1 | 10/2002 | Yi et al. | 424/426 |
| 2002/0161346 A1 | 10/2002 | Lockwood et al. | |
| 2002/0165581 A1 | 11/2002 | Brucker | |
| 2003/0015203 A1 | 1/2003 | Makower et al. | 128/831 |
| 2003/0040809 A1 | 2/2003 | Goldmann et al. | 623/23.76 |
| 2003/0072784 A1 | 4/2003 | Williams | 424/426 |
| 2003/0109855 A1 | 6/2003 | Solem et al. | |
| 2003/0158577 A1 | 8/2003 | Ginn et al. | |
| 2003/0208149 A1 * | 11/2003 | Coffey | 602/48 |
| 2003/0212357 A1 * | 11/2003 | Pace | 602/41 |
| 2003/0225347 A1 | 12/2003 | Argenta et al. | |
| 2004/0030304 A1 | 2/2004 | Hunt et al. | |
| 2004/0073151 A1 * | 4/2004 | Weston | 602/41 |
| 2004/0230179 A1 | 11/2004 | Shehada | |
| 2005/0065484 A1 | 3/2005 | Watson, Jr. | |
| 2005/0261780 A1 | 11/2005 | Heino et al. | |
| 2007/0185426 A1 | 8/2007 | Ambrosio et al. | |

FOREIGN PATENT DOCUMENTS

| | | |
|---|---|---|
| AU | 745271 | 4/1999 |
| AU | 755496 | 2/2002 |
| CA | 2005436 | 6/1990 |
| DE | 26 40 413 A1 | 3/1978 |
| DE | 40 37 931 A1 | 5/1992 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 307 180 | 5/1997 |
| GB | 2 333 965 A | 8/1999 |
| GB | 2336546 | 10/1999 |
| GB | 2 329 127 B | 8/2000 |
| JP | 4129536 | 4/1992 |
| SG | 71559 | 4/2002 |
| WO | WO 80/02182 | 10/1980 |
| WO | WO 87/04626 | 8/1987 |
| WO | WO 90/10424 | 9/1990 |
| WO | WO 93/09727 | 5/1993 |
| WO | WO 94/20041 | 9/1994 |
| WO | WO 96/05873 | 2/1996 |
| WO | WO 97/18007 | 5/1997 |
| WO | WO 99/13793 | 3/1999 |
| WO | WO 02/092783 | 11/2002 |
| WO | WO 03/028786 | 4/2003 |
| WO | WO 2004/047649 A1 | 6/2004 |

OTHER PUBLICATIONS

Susan Mendez-Eastmen, RN; "When Wounds Won't Heal" RN Jan. 1998, vol. 61 (1); Medical Economics Company, Inc., Montvale, NJ, USA; pp. 20-24.

James H. Blackburn, II, MD, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sept. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, May 2, 1986, pp. 42-46, and 7 page English translation thereof.

Davydov, Yu. A., et al; "Concepts for the Clinical-Biological Management of the Wound Process in the Treatment of Purulent Wounds by Means of Vacuum Therapy";Vestnik Khirurgi, Jul. 7, 1980, pp. 132-136, and 8 page English translation thereof.

N.A. Bagautdinov, "Variant of External Vacuum Aspiration in the Treatment of Purulent Diseases of the Soft Tissues," *Current Problems in Modern Clinical Surgery: Interdepartmental Collection*, edited by V. Ye Volkov et al. (Chuvashia State University, Cheboksary, U.S.S.R. 1986);pp. 94-96 (certified translation).

K.F. Jeter, T.E. Tintle, and M. Chariker, "Managing Draining Wounds and Fistulae: New and Established Methods," *Chronic Wound Care*, edited by D. Krasner (Health Management Publications, Inc., King of Prussia, PA 1990), pp. 240-246.

G.Živadinović, V. Dukić, Ž. Maksimović, D. Radak, and P. Peška, "Vacuum Therapy in the Treatment of Peripheral Blood Vessels," *Timok Medical Journal* 11 (1986), pp. 161-164 (certified translation).

F.E. Johnson, "An Improved Technique for Skin Graft Placement Using a Suction Drain," *Surgery, Gynecology, and Obstetrics* 159 (1984), pp. 584-585.

A.A. Safronov, Dissertation Abstract, *Vacuum Therapy of Trophic Ulcers of the Lower Leg with Simultaneous Autoplasty of the Skin* (Central Scientific Research Institute of Traumatology and Orthopedics, Moscow, U.S.S.R 1967) (certified translation).

M. Schein, R. Saadia, J.R. Jamieson, and G.A.G. Decker, "The 'Sandwich Technique' in the Management of the Open Abdomen," *British Journal of Surgery* 73 (1986), pp. 369-370.

D.E. Tribble, An Improved Sump Drain-Irrigation Device of Simple Construction, *Archives of Surgery* 105 (1972) pp. 511-513.

M.J. Morykwas, L.C. Argents, E.I. Shelton-Brown, and W. McGuirt, "Vacuum-Assisted Closure: A New Method for Wound Control and Treatment: Animal Studies and basic Foundation," *Annals of Plastic Surgery* 38 (1997), pp. 553-562 (Morykwas I).

C.E. Tennants, "The Use of Hypermia in the Postoperative Treatment of Lesions of the Extremities and Thorax," *Journal of the American Medical Association* 64 (1915), pp. 1548-1549.

Selections from W. Meyer and V. Schmieden, *Bier's Hyperemic Treatment in Surgery, Medicine, and the Specialties: A Manual of Its Practical Application*, (W.B. Saunders Co., Philadelphia, PA 1909), pp. 17-25, 44-64, 90-96, 167-170, and 210-211.

Chariker, Mark E., M.D., et al; "Effective Management of incisional and cutaneous fistulae with closed suction wound drainage"; Contemporary Surgery, vol. 34, Jun. 1989, pp. 59-83.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressin Allowing Continuous Treatment of a Biosurface", IRCS Medical Science: Biomedical Technology, Clinical Medicine, Surgery and Transplantation, vol. 7, 1979, p. 221.

Svedman, P. et at: "A Dressing System Providing Fluid Supply and Suction Drainage Used for Continuous or Intermittent Irrigation", Annals of Plastic Surgery, vol. 17, No. 2, Aug. 1986, pp. 125-133.

Online encyclopedia article, polyacrylonitrile. Http://en/wikipedia.org/wiki/Polyacrylonitrile. Accessed Jul. 13, 2008.

Online encyclopedia article, acrylonitrile. Http://en/wikipedia.org/wiki/Acrylonitrile. Accessed Jul. 13, 2008.

Ametek Product Bulletin, Model No. 116763-13; Mar. 1998.

Non-Final Office Action date mailed Feb. 27, 2007 for U.S. Appl. No. 10/818,454.

Response filed Mar. 6, 2007 to Non-Final Office Action date mailed Feb. 27, 2007 for U.S. Appl. No. 10/818,454.

Non-Final Office Action date mailed May 7, 2007 or U.S. Appl. No. 10/818,454.

Response filed Oct. 25, 2007 to Non-Final Office Action date mailed May 7, 2007 or U.S. Appl. No. 10/818,454.

Final Office Action date mailed Dec. 26, 2007 or U.S. Appl. No. 10/818,454.

Pre-Appeal Brief filed Mar. 24, 2008 or U.S. Appl. No. 10/818,454.

Notice of panel Decision from Pre-Appeal Brief Review date mailed May 15, 2008 or U.S. Appl. No. 10/818,454.

Appeal Bried filed Jun. 16, 2008 or U.S. Appl. No. 10/818,454.

Examiner's Answer to Appeal Brief date mailed Sep. 15, 2008 or U.S. Appl. No. 10/818,454.

Non-Final Office Action date mailed Feb. 28, 2003 for U.S. Appl. No. 09/996,970.

Response filed May 28, 2003 to Non-Final Office Action date mailed Feb. 28, 2003 for U.S. Appl. No. 09/996,970.

Notice of Allowance date mailed Jul. 1, 2003 for U.S. Appl. No. 09/996,970.

Non-Final Office Action date mailed Jun. 20, 2005 for U.S. Appl. No. 10/715,164.

Response filed Nov. 21, 2005 to Non-Final Office Action date mailed Jun. 20, 2005 for U.S. Appl. No. 10/715,164.

Final Office Action date mailed Mar. 28, 2006 for U.S. Appl. No. 10/715,164.

Response filed Sep. 28, 2006 to Final Office Action date mailed Mar. 28, 2006 for U.S. Appl. No. 10/715,164.

Non-Final Office Action date mailed Dec. 8, 2006 for U.S. Appl. No. 10/715,164.

Response filed Mar. 8, 2007 to Non-Final Office Action date mailed Dec. 8, 2006 for U.S. Appl. No. 10/715,164.

Final Office Action date mailed Jun. 5, 2007 for U.S. Appl. No. 10/715,164.

Response filed Aug. 6, 2007 to Final Office Action date mailed Jun. 5, 2007 for U.S. Appl. No. 10/715,164.

Advisory Action date mailed Sep. 27, 2007 for U.S. Appl. No. 10/715,164.

RCE and Response filed Oct. 30, 2007 to Final Office Action date mailed Jun. 5, 2007 for U.S. Appl. No. 10/715,164.

Non-Final Office Action date mailed Jan. 29, 2008 for U.S. Appl. No. 10/715,164.

Response filed Apr. 29, 2008 to Non-Final Office Action date mailed Jan. 29, 2008 for U.S. Appl. No. 10/715,164.

Final Office Action date mailed Oct. 20, 2008 for U.S. Appl. No. 10/715,164.

Non-Final Office Action date mailed Mar. 19, 2007 for U.S. Appl. No. 11/004,586.

Response filed Aug. 20, 2007 to Non-Final Office Action date mailed Mar. 19, 2007 for U.S. Appl. No. 11/004,586.

Non-Final Office Action date mailed Oct. 18, 2007 for U.S. Appl. No. 11/004,586.

Response filed Mar. 18, 2008 to Non-Final Office Action date mailed Oct. 18, 2007 for U.S. Appl. No. 11/004,586.

Final Office Action date mailed Jul. 17, 2008 for U.S. Appl. No. 11/004,586.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

RCE/Response filed Feb. 20, 2009 to Final Office Action date mailed Dec. 26, 2007 for U.S. Appl. No. 10/818,454.

Non-Final Office Action date mailed Apr. 24, 2009 for U.S. Appl. No. 10/818,454.

RCE/Response filed Jan. 21, 2009 to Final Office action date mailed Oct. 20, 2008 for U.S. Appl. No. 10/715,164.

Notice of Abandonment date mailed Mar. 18, 2009 for U.S. Appl. No. 11/004,586.

RCE/Response filed Jan. 7, 2010 to Final Office Action date mailed Oct. 7, 2009 in U.S. Appl. No. 10/818,454.

Examiner Interview Summary date mailed Jan. 12, 2010 in U.S. Appl. No. 10/818,454.

Response filed Feb. 16, 2010 to Non-Final Rejection date mailed Nov. 6, 2009 in U.S. Appl. No. 10/715,164.

European Official Action date mailed Aug. 29, 2008 in European Application No. 04 783 527.7-1526.
V.A.C.® Therapy Clinical Guidelines: A Reference Source for Clinicians (Jul. 2007).
Response filed Jun. 30, 2009 to Non-Final Office Action date mailed Apr. 24, 2009 for U.S. Appl. No. 10/818,454.
Restriction Requirement date mailed Jun. 4, 2009 for U.S. Appl. No. 10/715,164.
Response filed Jun. 30, 2009 to Restriction Requirement date mailed Jun. 4, 2009 for U.S. Appl. No. 10/715,164.
USPTO Final Office Action date mailed Oct. 7, 2009 in U.S. Appl. No. 10/818,454.
USPTO Non-Final Rejection date mailed Nov. 6, 2009 in U.S. Appl. No. 10/715,164.
Final Action date mailed May 19, 2010 in U.S. Appl. No. 10/715,164.
Non-Final Action date mailed Jun. 3, 2010 in U.S. Appl. No. 10/818,454.

* cited by examiner

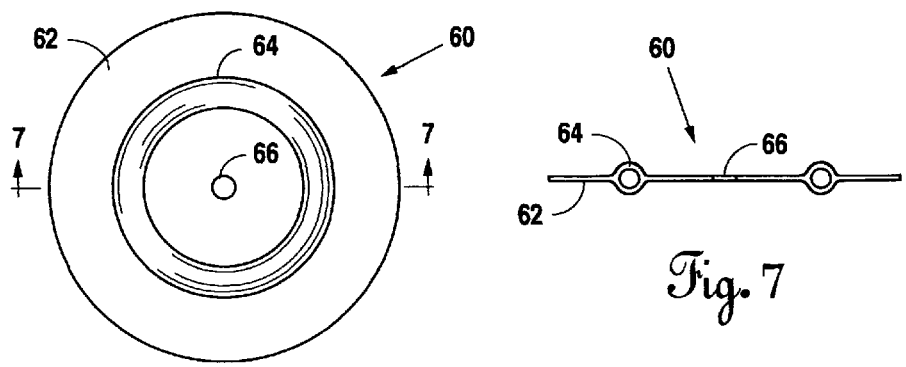
Fig. 6
Fig. 7
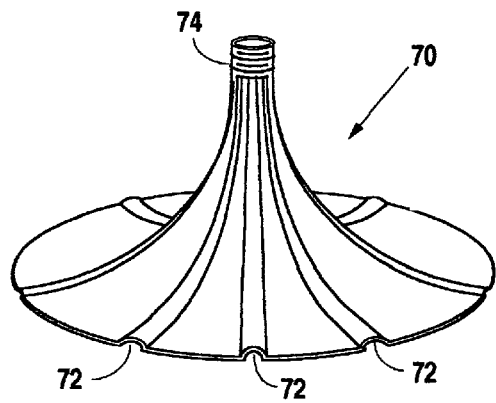
Fig. 8
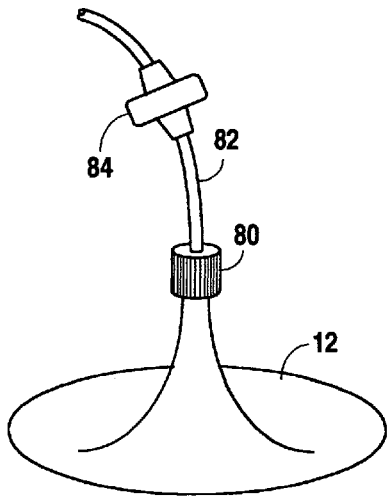
Fig. 9

WOUND DRESSING WITH ABSORPTION AND SUCTION CAPABILITIES

BACKGROUND OF THE INVENTION

This invention relates generally to the wound healing arts, and more particularly to a novel wound healing apparatus for removing excess fluid from a wound by absorbing the fluid into the dressing or suctioning the fluid through the dressing and out of the wound.

SUMMARY OF THE INVENTION

The present invention is directed to a wound dressing having a suction member adaptable for connection to a source of vacuum pressure and a semi-permeable cover overlying the suction member for attaching the dressing to a patient's skin surrounding a wound. The semi-permeable cover allows the wound to breathe while protecting the wound from undesirable substances such as bacteria, viruses, or fluids. When connected to a source of vacuum pressure, the suction member removes excess fluid from the wound and the semi-permeable cover facilitates circulation of sterile air in the wound, both of which promote healing of the wound. The wound dressing preferably has a hydrophobic or biodegradable base layer and one or more absorptive layers for absorbing fluid from the wound. The absorptive layers are preferably quilted with patches containing desiccant, adsorbent, or absorbent material. When the absorptive layers become saturated with fluid, they may be removed from the wound and replaced with fresh absorptive layers. Alternatively, the wound dressing may have one or more semi-absorbent stabilizing layers that allow fluid to pass through the suction member. If fluid is allowed to pass through the suction member, a fluid lock is preferably provided downstream from the suction member to prevent fluid from reaching the source of vacuum pressure. Any of the base layers, absorptive layers, or stabilizing layers may have medicine embedded therein to further promote healing.

A bladder is preferably provided with the dressing for distributing contact pressure away from the wound. Various sensors may be provided in the wound dressing for sensing various physiological parameters in the wound, such as oxygen saturation, blood pressure, respiratory rate, blood glucose, carbon dioxide due to infection, ECG activity, and serous fluid turbidity. The dressing may have electrical leads for providing electrical stimulation to the wound. Medicine may also be applied to the wound through one or more conduits in the wound dressing. This invention may be used with animals as well as humans.

BRIEF DESCRIPTION OF THE DRAWINGS

FIG. 6 is a top view of a wound dressing cover with an air bladder in accordance with the present invention.

FIG. 7 is a cross-sectional view of the wound dressing cover of FIG. 6 taken in the direction of arrows 7-7.

FIG. 8 is a perspective view of an alternative suction member in accordance with the present invention.

FIG. 9 is a perspective view of a suction member in accordance with the present invention connected to a fluid line having an in-line fluid lock.

DETAILED DESCRIPTION OF A PREFERRED EMBODIMENT

Figure 1:
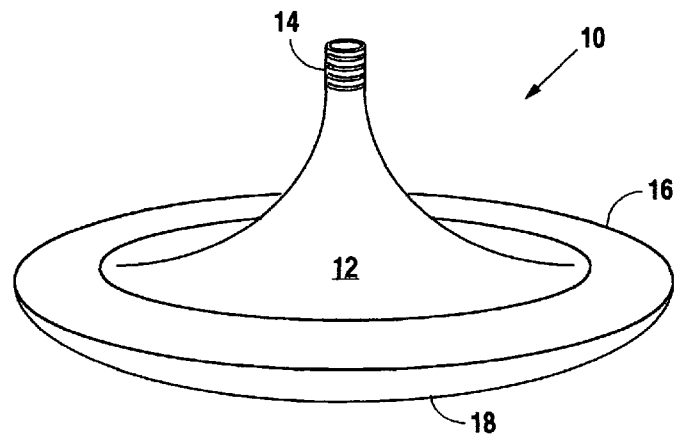
FIG. 1 is a perspective view of a wound dressing in accordance with the present invention.
Figure 2:
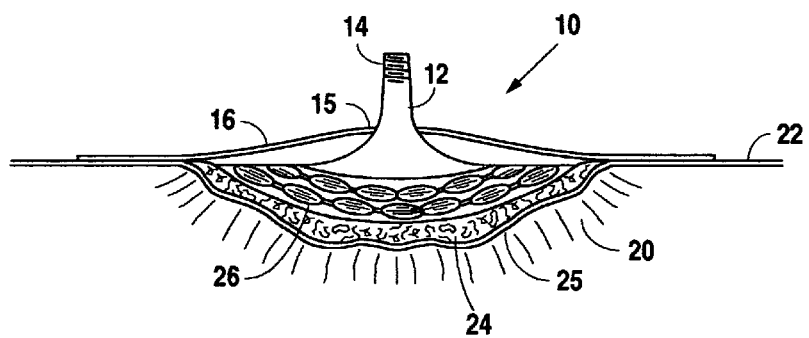
FIG. 2 is a side view of the wound dressing of FIG. 1 applied to a wound.
Figure 16:
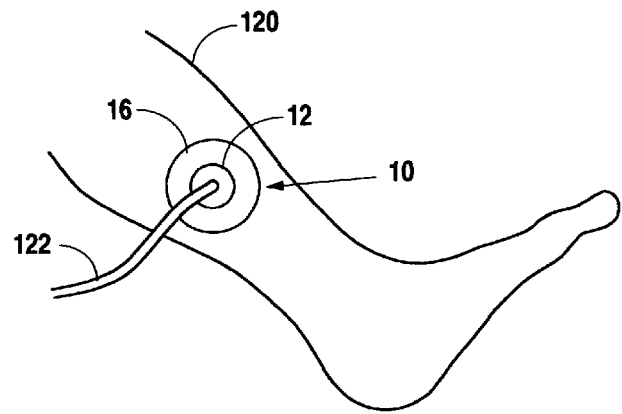
FIG. 16 is a top view of the wound dressing of FIG. 1 applied to a leg wound.

Referring to FIGS. 1 and 2, a wound dressing 10 in accordance with the present invention preferably comprises a suction member 12 having a fitting 14 for attachment to a source of vacuum pressure via a suction tube (not shown) and a plurality of dressing layers 24 and 26. As described further below, wound dressing 10 is designed to absorb excess fluid in a wound crater 25 in the flesh 20 of a patient. Fitting 14 may comprise threads, or part of a quick connect fitting, or any other suitable means for connecting suction member 12 to a source of vacuum pressure. Wound dressing 10 preferably has a porous base layer 24 for placement in the bottom of wound crater 25. Base layer 24, which is in direct contact with the flesh 20, preferably comprises a hydrophobic material, a biodegradable material, or a combination of both a hydrophobic material and a biodegradable material. Examples of suitable hydrophobic materials include petroleum-based plastics, polyester, nylon, and polyvinylchloride (PVC), but other hydrophobic materials could also be used. Examples of suitable biodegradable materials, which are absorbable into the human body, include synthetic materials such as coated VICRYL RAPIDE™ (polyglactin 910) sutures available from Ethicon (Somerville, N.J.), which may be woven into a mesh fabric or other suitable form. When placed inside the body, such biodegradable material typically absorbs into the body within about 5 to 10 days. As the material is being absorbed, it serves as a framework for fibroblasts to bridge the gap in the wounded tissue and thereby promote healing. Of course, other biodegradable materials could also be used in accordance with the present invention. For example, other suitable biodegradable materials include biodegradable plastics such as beta glucan available from Biopolymer Engineering, Inc. (Eagan, Minn.), which is an extract from brewer's yeast and also serves as an anti-infectant; polyhydroxyalkanoates (PHAs) available from Degradable Solutions AG (Zurich, Switzerland); and hard gelatins such as those used for ingestible capsules available from Capsugel™, a subsidiary of Pfizer, Inc. (Morris Plains, N.J.). Base layer 24 allows fluid in the wound crater 25 to flow upward through base layer 24 into one or more absorptive layers 26 under the influence of vacuum pressure supplied through suction member 12, which sits atop the uppermost absorptive layer 26. Base layer 24 thus promotes a certain degree of dryness at the base of the wound, which promotes healing. Absorptive layers 26 preferably comprise a fluid trapping agent, such as a desiccant, an adsorbent, an absorbent, or a combination thereof, to trap the fluid in the wound crater 25 and thereby assist in healing the wound. Layers 24 and 26 may be separate pieces or may be part of a unit 18, which may be attached to suction member 12 or separate. A semi-permeable cover 16 is placed over suction member 12, which protrudes through an opening 15 in cover 16. The underside of cover 16 preferably has an adhesive material, preferably with a peel-off backing, for fastening the wound dressing 10 to the skin 14 of the patient. Semi-permeable cover 16 preferably allows air to pass through it so that the wound can breathe, which aids the healing process, but does not allow undesirable things, such as liquids, bacteria, or viruses, to pass through. As used herein, "semi-permeable" means any material that allows one or more substances to pass through it but does not allow one or more other substances to pass through it. One example of a suitable semi-permeable material is Gore-Tex™ available from W. L. Gore & Associates, Inc., but other semi-permeable materials may also be used. Semi-permeable cover 16 thus facilitates circulation of sterile airflow to the wound in cooperation with suction member 12 and the source of vacuum pressure (not shown) to promote healing. An example of the application of wound dressing 10 to a leg wound is shown in FIG. 16, wherein cover 16 is used to attach wound dressing 10 to a wound on a leg 120, and a tube 122 connects suction member 12 to a source of vacuum pressure (not shown).

Figure 18:
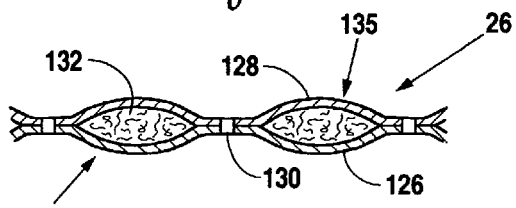
FIG. 18 is a cross-sectional view of a quilted fluid absorption layer in accordance with the present invention.

As shown in FIG. 18, each absorptive layer 26 preferably comprises an upper sheet 128 and a lower sheet 126 of fabric material, such as a fine woven cotton/polyester blend, quilted together with a trapping agent 132 in between, which forms a plurality of patches 135. Upper sheet 128 and lower sheet 126 may be quilted together by any suitable means, such as stitching or heat sealing. Preferably, sheets 128 and 126 are quilted together by heat sealing so that the seams may be perforated with holes 130, which allows better distribution of the vacuum pressure across the wound dressing and also facilitates tearing of the layer 26 by medical personnel in order to appropriately size the layer 26 for a given wound.

Figure 3:
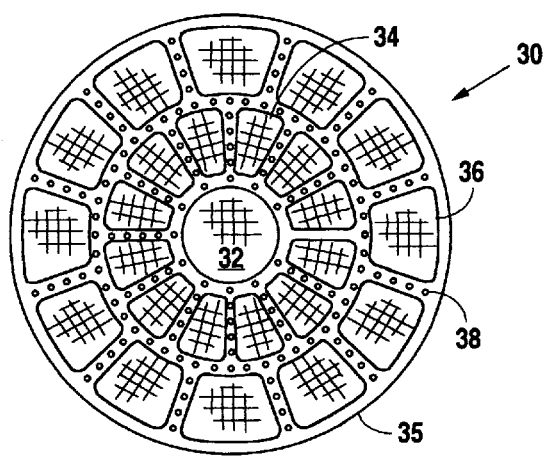
FIG. 3 is a top view of a circular quilted fluid absorption layer in accordance with the present invention.
Figure 4:
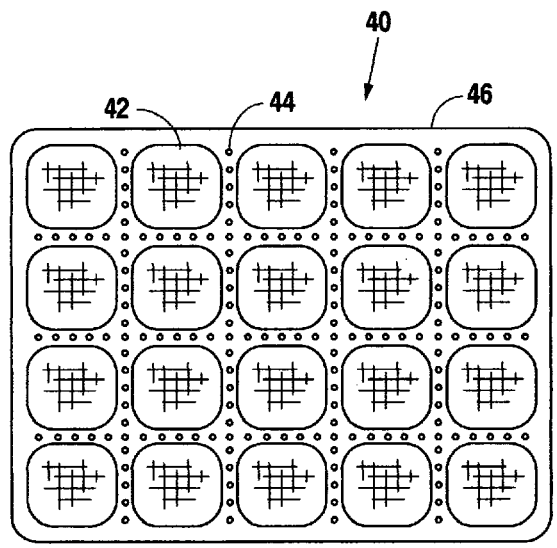
FIG. 4 is a top view of a rectangular quilted fluid absorption layer in accordance with the present invention.

Referring to FIG. 3, a round absorptive layer 30 is shown having a central patch 32 and a plurality of concentric quilted rings in material 35 formed by perforations 38. The patches 34, 36 of the various rings may be of uniform size or nonuniform size, as desired. Although the rings of FIG. 3 are shown as being of substantially uniform dimension in the radial and circumferential directions, persons of ordinary skill in the art will appreciate that other configurations could be utilized. Layer 30 is preferably constructed like layer 26 as discussed above in connection with FIG. 18 such that patches 32, 34, 36 contain a trapping agent (not shown). Perforations 38 facilitate the sizing of layer 30 to the desired diameter. If desired, layer 30 could also be torn along the radial perforations, which could be aligned instead of staggered as shown in FIG. 3. An alternative rectangular absorptive layer 40 is shown in FIG. 4 having patches 42 formed in material 46 by perforations 44. Persons of skill in the art will recognize that many other shapes are possible in accordance with the present invention.

Figure 5:
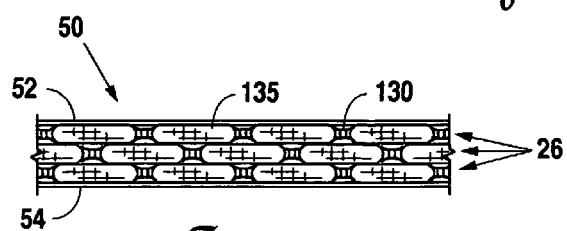
FIG. 5 is a side view of a plurality of quilted fluid absorption layers in accordance with the present invention.

FIG. 5 shows a pad 50 comprising three absorptive layers 26 held between an upper sheet 52 and a lower sheet 54. More or fewer layers 26 could be used, depending on the desired thickness of the pad 50. The layers 26 are preferably arranged so that the patches 135 and holes 130 of the respective layers 26 are not aligned, which promotes a more uniform distribution of the vacuum pressure throughout the wound dressing.

Figure 17:
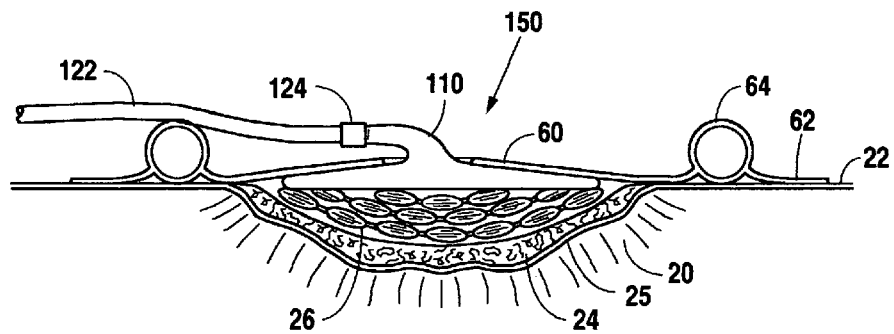
FIG. 17 is a side view of another alternative embodiment of a wound dressing in accordance with the present invention applied to a wound.

FIGS. 6 and 7 show an alternative semi-permeable cover 60 having an air bladder 64 for relieving the patient from contact pressure at the wound site. As illustrated in FIG. 17, air bladder 64 has a larger diameter than the wound so that if the patient presses against a surface, such as a bed mattress, in the vicinity of the wound, the contact pressure will be distributed away from the wound, which enhances patient comfort and is especially useful for treating pressure ulcers. Cover 60 has a central opening 66 for allowing a suction member to pass through and an outer portion 62 having an adhesive on the underside for attaching cover 60 to the skin of the patient about the wound. Persons of skill in the art will appreciate that shapes other than a circle may be used for cover 60 and air bladder 64. Additionally, although bladder 64 is preferably filled with air for the sake of simplicity, bladder 64 may be filled with another suitable fluid, such as a gas other than air or a liquid. Also, although bladder 64 is preferably integral to cover 60, bladder 64 may be separate from cover 60.

As mentioned above, wound dressing 10 of FIG. 1 is designed to remove fluid from the wound by absorbing excess fluid in the wound crater 25 rather than sucking fluid out of the wound through the suction member 12. When dressing 10 reaches its fluid absorption capacity, it may be removed from the wound and replaced with a fresh dressing 10. Dressing 10 may be replaced in its entirety if it is made as a single unit, or the absorptive layer(s) 26 and perhaps the base layer 24 may be replaced separately, as desired. As shown in FIG. 9, suction member 12 of dressing 10 is preferably connected via connector 80 to a tube 82 having an in-line fluid lock 84 downstream from suction member 12 between dressing 10 and the source of vacuum pressure (not shown). Fluid lock 84, which is well known in the art, serves to block off tube 82 if it senses any fluid so that no fluid will reach the source of vacuum pressure. Accordingly, the source of vacuum pressure need not have a means for absorbing fluid, which reduces cost, simplifies the construction and maintenance of the source of vacuum pressure, and enhances sanitation of the source of vacuum pressure. Although fluid lock 84 is shown separate from suction member 12, fluid lock 84 may be incorporated into suction member 12, if desired.

Figure 10:
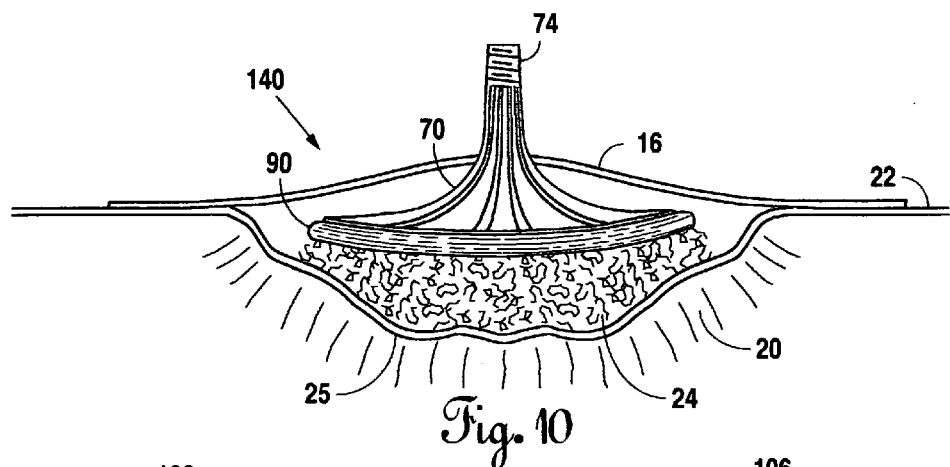
FIG. 10 is a side view of an alternative embodiment of a wound dressing in accordance with the present invention applied to a wound.

FIG. 10 illustrates an alternative wound dressing 140 having a base layer 24 in the wound crater 25 comprising a hydrophobic material, a biodegradable material, or a combination thereof like dressing 10 described above. However, unlike dressing 10, dressing 140 has no absorptive layer. Instead, a stabilizing layer 90 is placed on top of base layer 24. Stabilizing layer 90 preferably comprises a semi-absorbent material, such as gauze, but no desiccant. Thus, stabilizing layer 90 allows fluid to flow through it. An alternative suction member 70 is placed on top of stabilizing layer 90. As shown in FIG. 8, suction member 70 has a plurality of channels 72 formed on its underside that assist in evenly distributing the vacuum pressure about the wound site. Suction member 70 also has a fitting 74 for connection to a source of vacuum pressure. A semi-permeable cover 16 having adhesive on its underside is placed over suction member 70 to secure dressing 140 to the skin 22 of the patient about the wound. Because fluid is allowed to flow through dressing 140, the vacuum source used with this embodiment should have the ability to absorb the fluid. A preferred vacuum source for use with dressing 140 is a personally portable vacuum desiccator as described in U.S. Pat. No. 6,648,862 issued to the present inventor, which is incorporated herein by reference.

Figure 11:
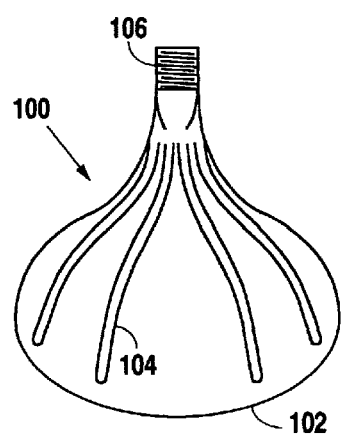
FIG. 11 is a top view of another alternative suction member in accordance with the present invention.
Figure 12:
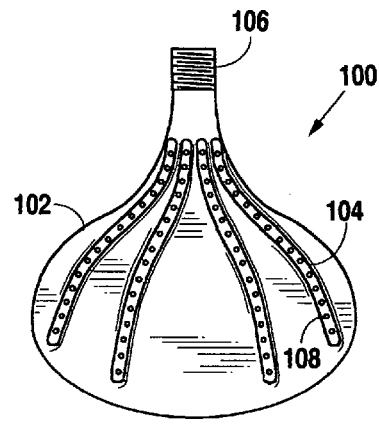
FIG. 12 is a bottom view of the suction member of FIG. 11.
Figure 13:
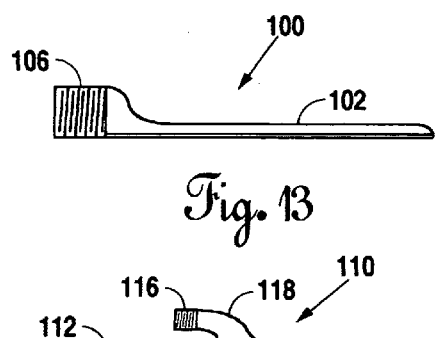
FIG. 13 is a side view of the suction member of FIG. 11.

FIGS. 11-13 illustrate another alternative suction member 100 having a bulbous body 102 with a plurality of channels 104 formed on its underside. Channels 104 may be open channels, or channels 104 may comprise tubes having a plurality of fenestrations 108 therein to assist in distributing the vacuum pressure about the wound site. Suction member 100 has a fitting 106 that is on the perimeter rather than centrally located as in suction members 12 and 70 described above, which may be more desirable in some wound applications. Additionally, fitting 106 is pointed in a direction that will lie substantially parallel to the skin of the patient when installed, which makes for a lower profile than suction members 12 and 70 described above.

Figure 20:
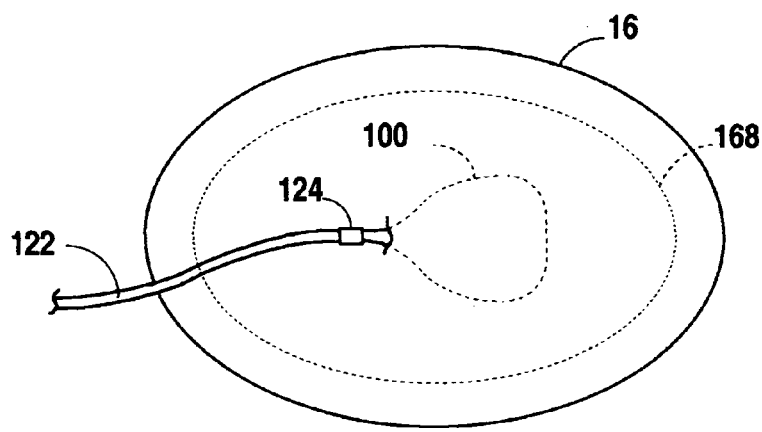
FIG. 20 is a top view of the suction member of FIG. 11 installed beneath a semi-permeable cover.

FIG. 20 illustrates suction member 100 installed beneath a semi-permeable cover 16. A tube 122 is attached to fitting 106 (not shown) of suction member 100, which extends through an opening in the cover 16, with a connector 124. Tube 122 is connected to a source of vacuum pressure (not shown). An adhesive is preferably provided on the underside of cover 16 to facilitate attachment of cover 16 to the patient's skin surrounding the wound. If desired, the adhesive may be provided only about the perimeter of cover 16 as indicated by dashed line 168, and perhaps on the portion of cover 16 that interfaces with suction member 100, rather than the entire underside of cover 16, which helps facilitate aspiration of the wound about the periphery of the wound.

Figure 14:
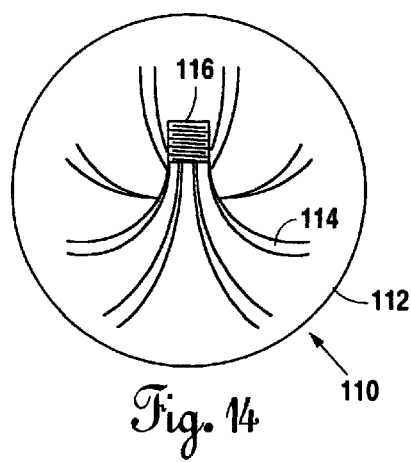
FIG. 14 is a top view of yet another alternative suction member in accordance with the present invention.
Figure 15:
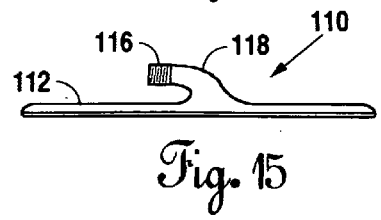
FIG. 15 is a side view of the suction member of FIG. 14.

FIGS. 14 and 15 illustrate still another suction member 110 having a centrally located attachment fitting 116 that is oriented to lie substantially parallel to the skin of the patient when installed, which also makes for a lower profile than suction members 12 and 70 described above. Suction member 110 has a circular base 112 with a central plenum 118 leading to fitting 116. Base 112 preferably has a plurality of channels 114 on its underside to assist in distributing the vacuum pressure.

FIG. 17 illustrates a wound dressing 150 comprising a base layer 24 as described above, a plurality of absorptive layers 26 for absorbing fluid from the wound, a suction member 110, and a semi-permeable cover 60 having an air bladder 64 as described above. Suction member 110 is connected to a source of vacuum pressure (not shown) via a tube 122 and connector 124. Dressing 150 provides a lower profile due to the configuration of suction member 110.

Figure 19:
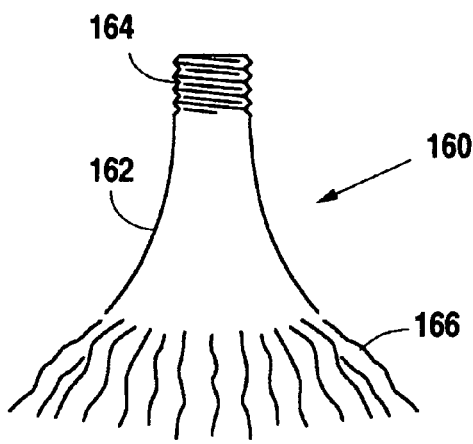
FIG. 19 is a side view of another alternative embodiment of the present invention.

FIG. 19 illustrates another embodiment of a wound dressing 160 in accordance with the present invention in which at least a portion of the suction member itself is bioabsorbable. Dressing 160 has a suction member 162 with a fitting 164 for attachment to a source of vacuum pressure similar to the embodiments discussed above, but the lower portion of suction member 162 has a plurality of bioabsorbable filaments 166 which are absorbed by the body when dressing 160 is installed in a wound. Filaments 166 are preferably made of a bioabsorbable plastic, a soy-based material, or a glyco-protein material. Examples of suitable materials for filaments 166 include beta glucans, PHAs, and hard gelatins such as those used on ingestible capsules. Suction member 162 and filaments 166 may be made of the same material, or suction member 162 may be made of a different material than filaments 166. Dressing 160 is preferably installed with a semi-permeable cover 16 like the embodiments discussed above. Dressing 160 may be used by itself or in conjunction with a porous base layer, an absorptive layer, a stabilizing layer, or a combination thereof.

Figure 21:
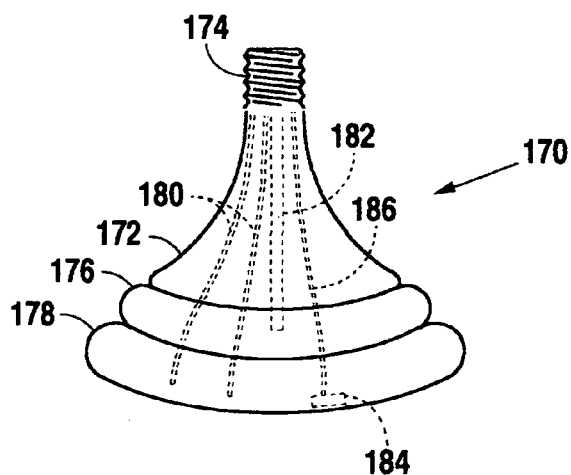
FIG. 21 is a side view of yet another alternative embodiment of the present invention.

FIG. 21 illustrates another alternative wound dressing 170 having a suction member 172 with an absorptive layer 176 and a porous base layer 178 attached to the bottom of the suction member 172. Similar to the embodiments discussed above, a fitting 174 is provided for connection to a source of vacuum pressure via a suction tube (not shown). One or more electrical leads 180 are provided in wound dressing 170 to facilitate electrical stimulation of the wound as an additional means of promoting healing as is known in the art. Electrical leads 180 preferably extend through the suction member 172 and are connected to a source of electrical energy (not shown), preferably either as part of or in the vicinity of the dressing 170 or at or near the source of vacuum pressure. One or more conduits 182 may also be provided in dressing 170 to facilitate the administration of medicine directly to the wound. For example, antibiotics, angiogenic factors, keratin, or other suitable medicines may be provided through conduits 182, which preferably extend through the suction member 172. Alternatively, suitable medicines may be embedded in dressing 170, such as in base layer 178 or absorptive layer 176. For example, a conventional antibiotic such as ciprofloxacin or a lyophilized (freezedried) antibiotic that becomes activated upon contact with moisture may be embedded in the dressing to help promote healing. Such embedded antibiotics also help to render the respective dressing layers nonbiohazardous after the wound fluids are absorbed therein. Similarly, a keratin-based substance or an angiogenic substance may be embedded in the dressing to help promote healing and stimulate the creation of new blood vessels. Additionally, one or more sensors 184 and associated signal lines 186 may be provided in dressing 170 to monitor any of a number of various physiological parameters. For example, sensor 184 may comprise one or more of an oxygen saturation ($SaO_2$) sensor, a blood pressure sensor, a respiratory rate sensor, a blood glucose sensor, a carbon dioxide ($CO_2$) sensor, or a serous fluid turbidity sensor, or a combination thereof, as is known in the art. Electrical leads 180, conduits 182, and signal lines 186 preferably extend through fitting 174 and the suction tube to their respective electrical energy source, medicine source, or signal processor (not shown). Although sensor 184 is illustrated as being in the base layer 178 of the dressing, sensor 184 may be located in an intermediate or upper layer of the dressing, depending on the sensor type and the particular application. For sensing blood pressure, sensor 184 preferably comprises a micro pressure transducer such as a Mikro-Tip™ SPR series pressure transducer available from Millar Instruments, Inc. (Houston, Tex.) or an Accutorr Plus™ sensor available from Datascope Corporation (Montvale, N.J.).

Figure 22:
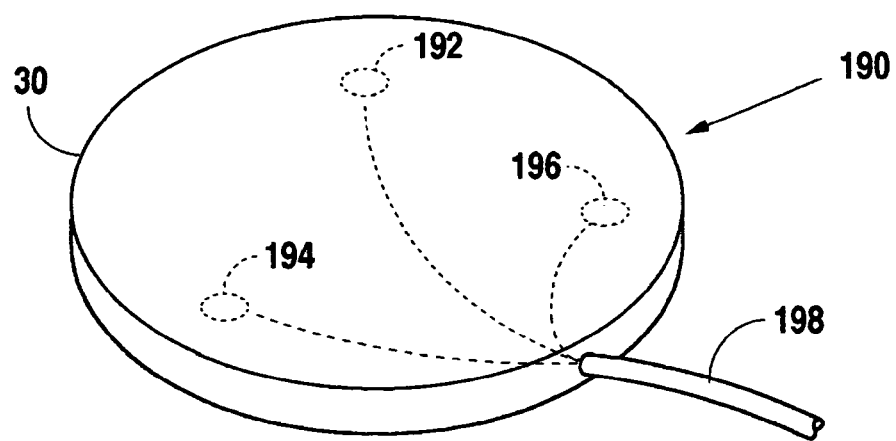
FIG. 22 is a schematic perspective view of an absorptive layer having an ECG sensor in accordance with the present invention.

FIG. 22 illustrates an example of a sensor pad 190 comprising an absorptive layer 30 as described above with an ECG sensor embedded therein. The ECG sensor preferably has three electrodes 192, 194, 196 in spaced relation to one another, each of which is connected by an electrical wire extending from cable 198. Sensor pad 190 may be used as an absorptive layer in a wound dressing with a suction member as described above. Cable 198 is preferably routed through a suction member and a suction tube as described above to an ECG processor (not shown). As is known in the art, electrodes 192, 194, 196 and the ECG processor may be used to monitor the electrical activity of a patient's heart. Thus, sensor pad 190 not only absorbs fluid from the wound in absorptive layer 30 but also conveniently provides ECG monitoring capability at the wound site. Persons of ordinary skill in the art will appreciate that an ECG sensor may also be imbedded in a base layer or a stabilizing layer as described above rather than an absorptive layer. Additionally, the ECG electrodes 192, 194, 196 may be used to measure the difference in bioimpedance of adjacent bodily tissue, such as the chest wall, when the patient is inhaling versus when the patient is exhaling and thereby calculate the patient's respiratory rate. Such calculations are preferably made by a computerized signal processor (not shown).

Figure 23:
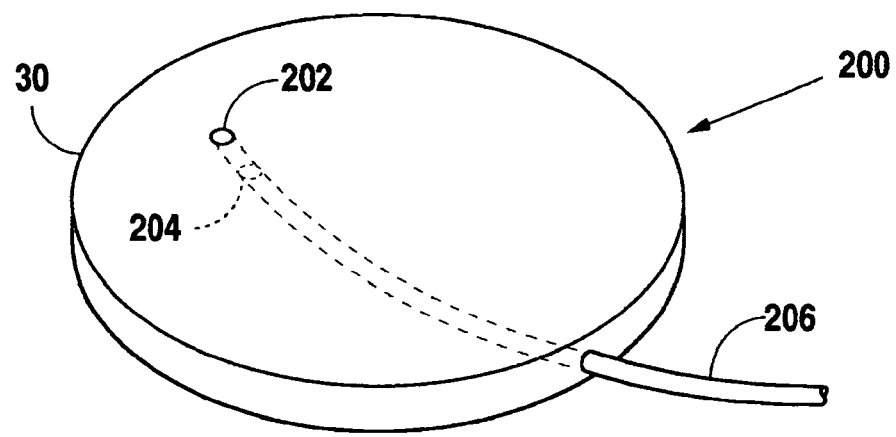
FIG. 23 is a schematic perspective view of an absorptive layer having an oxygen saturation sensor in accordance with the present invention.

FIG. 23 illustrates an example of a sensor pad 200 comprising an absorptive layer 30 as described above with an oxygen saturation ($SaO_2$) sensor embedded therein. As is known in the art, the oxygen saturation sensor preferably comprises a light source 202 and a light detector 204 served by an electrical cable 206. Sensor pad 200 may be used as an absorptive layer in a wound dressing with a suction member as described above. Cable 206 is preferably routed through a suction member and a suction tube as described above to an $SaO_2$ processor (not shown). Such an $SaO_2$ sensor and processor may be used to monitor the oxygen saturation level of the blood in the vicinity of the wound according to methods well known in the art. A preferred $SaO_2$ sensor is an Oxi-Max™ sensor available from NellCor Puritan Bennett, Inc. (St. Louis, Mo.). For best results, the $SaO_2$ sensor should be placed adjacent the flesh of the wound. Sensor pad 200 thus not only absorbs fluid from the wound in absorptive layer 30 but also conveniently provides $SaO_2$ monitoring capability at the wound site. Persons of ordinary skill in the art will appreciate that an $SaO_2$ sensor may also be imbedded in a base layer or a stabilizing layer as described above rather than an absorptive layer. Additionally, because the blood being monitored by the $SaO_2$ sensor is generally pulsing through blood vessels in the flesh at a certain frequency, the signal received by the detector 204 will be periodic, and the period of that signal is indicative of the patient's heart rate. Thus, the heart rate may be calculated from the $SaO_2$ signal, preferably by a computerized signal processor (not shown).

As is known in the art, PHA material degrades into $CO_2$ and water, and the rate of degradation is markedly increased by elevated levels of bacteria. Thus, if a wound containing PHA material is infected, the bacteria will break down the PHA material at a faster rate, which will increase the rate of production of $CO_2$. Accordingly, if a wound dressing in accordance with the present invention includes PHA material as discussed above, the dressing also preferably includes a $CO_2$ sensor as a means of monitoring the wound for infection. The $CO_2$ sensor may be provided either as part of the wound dressing itself or downstream as part of the suction tube or vacuum source that is connected to the wound dressing. The $CO_2$ sensor may provide a visual or audible indication if the $CO_2$ reaches or exceeds a certain predetermined level as is known in the art so that a caregiver may check the wound for infection. The YSI 8500 $CO_2$ sensor available from YSI Incorporated (Yellow Springs, Ohio) is an example of a suitable $CO_2$ sensor that is adaptable for use in accordance with the present invention.

Persons of ordinary skill in the art will appreciate that the various suction members disclosed herein may be used with either an absorptive dressing, such as dressing 10 described above, or a flow-through dressing, such as dressing 140 described above. Additionally, although the semi-permeable covers 16 and 60 described above preferably have an adhesive on the underside for attaching the dressing to the skin surrounding the wound, the dressing may be attached to the patient with a separate adhesive member overlapping the perimeter of the semi-permeable cover. Also, a wound dressing in accordance with the present invention comprising a suction member, a semi-permeable cover, and any desired base layers, absorptive layers, and stabilizing layers may be provided as an integrated unit rather than as separate pieces. Further, a wound dressing in accordance with the present invention, including the suction member if made of plastic or other suitable material, may be trimmed to fit any desired shape of wound. Additionally, any of the sensors described herein may be used with any of the dressings described herein.

Although preferred embodiments described herein preferably include one or more base layers, absorptive layers, or stabilizing layers as discussed above, a basic embodiment of the present invention may simply have a suction member and a semi-permeable cover overlying the suction member without any base layers, absorptive layers, or stabilizing layers. When connected to a source of vacuum pressure, the suction member effectively removes fluid from the wound and the semi-permeable cover facilitates circulation of sterile air to the wound, both of which promote healing of the wound. Likewise, the biodegradable or absorptive layers disclosed herein may be used to advantage to help heal wounds without a suction member or a semi-permeable cover.

Although the foregoing specific details describe a preferred embodiment of this invention, persons reasonably skilled in the art will recognize that various changes may be made in the details of this invention without departing from the spirit and scope of the invention as defined in the appended claims. Therefore, it should be understood that this invention is not to be limited to the specific details shown and described herein.

I claim:

1. A method of treating a wound, comprising:
   applying a suction member to the wound;
   covering said suction member with a semi-permeable cover;
   fastening said cover to skin surrounding the wound; and
   connecting said suction member to a source of vacuum pressure to remove fluid from the wound;
   wherein said suction member comprises a plurality of bioabsorbable filaments.

2. The method of claim 1 further comprising applying at least one absorptive layer having a fluid trapping agent beneath said suction member.

3. The method of claim 2, wherein said at least one absorptive layer comprises a quilted material having a plurality of patches containing a fluid trapping agent.

4. The method of claim 3, wherein said quilted material comprises a plurality of perforations.

5. The method of claim 2, wherein said fluid trapping agent is selected from the group consisting of desiccant, adsorbent, and absorbent.

6. The method of claim 1 further comprising the step of providing at least one sensor for sensing at least one physiological parameter in the wound.

7. The method of claim 6, wherein said at least one sensor is selected from the group consisting of an oxygen saturation sensor, a blood pressure sensor, a respiratory rate sensor, a blood glucose sensor, a carbon dioxide sensor, an ECG sensor, and a serous fluid turbidity sensor.

8. The method of claim 1 further comprising the step of applying a porous base layer to a base of the wound beneath said suction member.

9. The method of claim 8, wherein said base layer comprises a material selected from the group consisting of hydrophobic material, biodegradable material, and a combination of hydrophobic material and biodegradable material.

10. The method of claim 1 further comprising the step of providing a bladder for distributing contact pressure outside the vicinity of the wound.

11. The method of claim 10, wherein said bladder is integral with said cover.

12. The method of claim 1, wherein said cover comprises an underside having an adhesive with a peel-off backing.

13. The method of claim 1 further comprising the step of providing electrical stimulation to the wound via electrical leads extending through said suction member.

14. The method of claim 1 further comprising the step of providing medicine to the wound via at least one conduit extending through said suction member.

15. The method of claim 1, wherein said semi-permeable cover is permeable to air and impermeable to at least one of liquids, viruses, and bacteria.

16. The method of claim 1 further comprising the step of trimming said suction member to fit the shape of the wound.

17. The method of claim 1 further comprising the step of providing a fluid lock to prevent fluid from being transmitted to said source of vacuum pressure.

18. The method of claim 1 further comprising the step of applying at least one stabilizing layer in the wound beneath said suction member wherein fluid is allowed to flow through said at least one stabilizing layer and said suction member.

19. The method of claim 1 further comprising:
  applying a porous base layer to a base of the wound beneath said suction member;
  applying at least one absorptive layer having a fluid trapping agent beneath said suction member; and
  wherein said porous base layer or said at least one absorptive layer comprises medicine embedded therein.

20. The method of claim 1, wherein the bioabsorbable filaments are made of a bioabsorbable plastic.

21. The method of claim 1, wherein the bioabsorbable filaments are made of a soy-based material.

22. The method of claim 1, wherein the bioabsorbable filaments are made of a glyco-protein material.

23. The method of claim 1, wherein the bioabsorbable filaments are beta glucans.

24. The method of claim 1, wherein the bioabsorbable filaments are gelatins.

25. The method of claim 1, wherein the bioabsorbable filaments are polyhydroxyalkanoates.

* * * * *